United States Patent
Canivenc et al.

(10) Patent No.: US 6,312,578 B1
(45) Date of Patent: Nov. 6, 2001

(54) METHOD FOR EXTRACTING AMINE COMPOUNDS FROM A LIQUID MEDIUM

(75) Inventors: Edith Canivenc, Lyons; Dominique Horbez, Franconville, both of (FR)

(73) Assignee: Rhodia Fiber & Resin Intermediates, Courbevoie Cedex (FR)

( * ) Notice: Subject to any disclaimer, the term of this patent is extended or adjusted under 35 U.S.C. 154(b) by 0 days.

(21) Appl. No.: 09/269,783
(22) PCT Filed: Oct. 3, 1997
(86) PCT No.: PCT/FR97/01760
§ 371 Date: Sep. 7, 1999
§ 102(e) Date: Sep. 7, 1999
(87) PCT Pub. No.: WO98/15341
PCT Pub. Date: Apr. 16, 1998

(30) Foreign Application Priority Data

Oct. 4, 1996 (FR) .................................................. 96 12327

(51) Int. Cl.⁷ .................................................... B01D 61/44
(52) U.S. Cl. ............................ 204/530; 204/541; 205/431
(58) Field of Search ............................. 205/431; 204/530, 204/541

(56) References Cited

U.S. PATENT DOCUMENTS 4,238,306  12/1980  Perry .

FOREIGN PATENT DOCUMENTS

| 36 27 280 | 2/1987 | (DE) . |
| 1 223 635 | 6/1960 | (FR) . |
| 1 267 568 | 6/1961 | (FR) . |
| 91 02584 | 3/1991 | (WO) . |

OTHER PUBLICATIONS

Ken–Ichi Kikuchi et al, "Separation of Amino of Amino by Electrodialysis with Ion–Exchange Membranes", Journal of Chemical Engineering of Japan, vol. 28, No. 1, Feb. 1, 1995, pp. 103–109, XP000502994.

*Primary Examiner*—Arun S. Phasge
(74) *Attorney, Agent, or Firm*—Burns, Doane, Swecker & Mathis, L.L.P.

(57) ABSTRACT

The invention concerns a method for extracting by electrodialysis a compound comprising at least amine functions capable of protonation from a liquid medium. More particularly it concerns a method for extracting, and separating at least the monomers comprising amine functions capable of protonation from a liquid medium derived from the hydrolysis of polyamides. The method of extraction from a liquid medium consists in subjecting to protonation the amine function(s) of the compounds to be extracted by adjusting the pH of the medium and in separating the compounds by passing them through a cationic membrane under the effect of an electric current. The invention is particularly applicable in processes for the chemical stabilisation of polyamides such as the PA 66 PA 6.

15 Claims, No Drawings

METHOD FOR EXTRACTING AMINE COMPOUNDS FROM A LIQUID MEDIUM

This application is a 371 of PCT/FR97/01760 filed Oct. 3, 1997.

The present invention relates to a process for extracting, by electrodialysis, a compound comprising at least protonatable amine functions from a liquid medium.

The invention relates more particularly to a process for extracting and separating at least the monomers comprising protonatable amine functions from a medium originating from the hydrolysis of polyamides.

Synthetic materials, and among these polymers containing amide functions such as polyamides and more particularly polyamide 6.6 or polyamide 6, are increasingly being used to make varied articles such as textile fibres, technical industrial yarns, filaments or moulded articles such as components for electricity, electronics or motor vehicles. These synthetic materials are generally used in the form of compositions comprising, in addition to the synthetic material, various additives for, for example, increasing their thermal stability, or their stability to radiation, or for improving their mechanical, electrical or electrostatic properties, dyes and pigments. These additives are of very varied nature and can be either organic or inorganic compounds.

In addition, in particular for the preparation of moulded articles, the compositions comprise fillers, often inorganic fillers, such as glass fibres, talc, clay, etc.

The materials thus produced can be destroyed after use. One of the standard methods of destruction is incineration, which allows the energy to be recovered. However, it is also proposed to recycle these materials.

In point of fact, one of the current preoccupations lies in the recycling of the products obtained from natural sources in order, on the one hand, to slow down the depletion of these sources, and, on the other hand, to reduce the volume of waste in nature.

Thus, processes for depolymerizing polyamides have been proposed. One of the processes consists in carrying out a hydrolysis in acidic, neutral or basic medium of the polyamide in order to obtain either oligomers with a low degree of polymerization, or salts. The hydrolysis process applies in particular to the depolymerization of PA 6-type polyamides, i.e. polyamides obtained by homopolycondensation of an amino acid or of a lactam.

In the case of PA 6.6-type polyamides, i.e. polyamides obtained by polymerization between diamine and a diacid, the hydrolysis must be carried out in alkaline medium in order to obtain total depolymerization. In the case of a hydrolysis in neutral medium, the hydrolysate medium contains a mixture of oligomers with a different degree of polymerization generally of between 2 and 40, and more specifically between 2 and 20.

Hydrolysis in alkaline medium presents a major drawback since it is necessary, in order to recover the acidic monomer, for example the adipic acid, to react the adipate formed with an acid, for example nitric acid. This process thus consumes product (acid) and generates an effluent (alkaline salts). In order to overcome this problem, an electrolytic process for converting the adipate salt into adipic acid has been proposed in International patent applications WO 93/25299, WO 93/25514 and WO 93/25513.

French patent applications FR 95/08916 and FR 95/08917 have also proposed a process for thermally hydrolysing polyamides in neutral medium, and then converting the oligomers thus obtained into amine, acid or amino acid monomers or into amine salts by enzymatic hydrolysis.

These compounds dissolved in the hydrolysis medium can be extracted and separated by various processes such as crystallization, precipitation or distillation. However, these conventional extraction and purification processes have low yields and are not very selective.

One of the aims of the present invention is to propose a process for selectively separating the various compounds produced, and in particular compounds comprising at least one protonatable amine function.

To this end, the invention proposes a process for extracting from a liquid medium a compound comprising at least one protonatable amine function, characterized in that it consists in protonating the amine function(s) by adjusting the pH of the medium and in separating the compounds by passing them through a cationic membrane under the effect of an electric current.

Thus, the electrodialysis elemental cell for carrying out the invention comprises a cationic membrane arranged between two electrodes.

According to another characteristic of the invention, the pH of the solution is determined and adjusted so as to correspond to the isoelectric point or to the pKa of the compound to be extracted by passing it through the cationic membrane, and more advantageously to the pKa of the amine to be separated.

The term "isoelectric point" will be used when the compound to be extracted comprises several positively and negatively ionizable functions, respectively, such as amine functions and acid functions.

Thus, the process of the invention makes it possible to separate different compounds contained in a liquid medium by selective extraction of one of the compounds, or by carrying out a separation in several steps with extraction of a compound at each step with modification of the pH of the liquid medium between each step in order to adapt it to the isoelectric point or pKa of the compound to be extracted in the said step.

In one preferred embodiment of the invention, in particular when the liquid medium comprises monomers produced by the depolymerization of polyamides, the elemental electrodialysis cell advantageously comprises a cationic membrane and an anionic membrane.

Thus, this cell comprises a dilution compartment D into which the liquid medium to be treated is fed, and two concentration compartments ($C^+$, $C^-$) in which the compounds extracted from the liquid medium and crossing the cationic and anionic membranes, respectively, under the effect of the electric current, are concentrated. When cells are mounted in electrical series, the compartment $C^+$ of one cell will also form the compartment $C^-$ of the adjacent cell in the series, and vice versa for the compartment $C^-$. Consequently, for greater clarity, all the concentration compartments will be referred to as C, without distinction of signs.

In point of fact, the process of the invention finds a preferential application in the separation and recovery of the monomers produced by a process of depolymerizing polyamides.

Thus, the hydrolysis of polyamide in neutral medium leads to an aqueous solution of diamine, diacid and/or amino acid monomers depending on the nature of the polyamides treated, as well as oligomers with a degree of polymerization of, for example, between 2 and 40.

The treatment of such a solution by the process of the invention makes it possible to extract and separate the diamine and diacid monomers from the oligomers and amino acids.

However, in order to improve the depolymerization yield and to convert the oligomers into monomers, the aqueous solution described above is subjected to an enzymatic hydrolysis.

Examples of enzymatic hydrolysis of polyamide oligomers, and more particularly of polyhexamethylene adipamide (PA 6.6) oligomers are described in French patent applications No. 95 08916 and No. 95 08917, the texts of which are incorporated into the present invention.

Briefly, the processes described consist in carrying out a thermal hydrolysis of polyamides in neutral medium, and then in treating this hydrolysate with enzymes known as "amidases". These enzymes are, for example, the one (PAM I) expressed by the *E. coli* strain containing the plasmid PXL 2564 filed at the National Collection of Culture and Microorganisms under No. I 1495, on Nov. 29, 1994, the enzyme produced by the strain nyl-B described in Kinoshita et al. (Eur. J. Biochem 116, 547–551, 1981), the amidase (PAM II) expressed by the strain Comonas acidovorans filed at the National Collection of Cultures and Microorganisms under No. I 1522 of Jan. 4, 1995.

The solution recovered after enzymatic hydrolysis contains only amine salts and/or diamine and diacid monomers, lactams or amino acids depending on the nature of the polyamides used.

The process of the invention makes it possible to extract the diamine monomers from such a medium, and in the case of an electrodialysis with cationic and anionic membranes, to extract, on the one hand, the protonated diamines across the cationic membrane, and, on the other hand, the diacid monomers across the anionic membrane, in the respective concentration compartments C.

The compounds, such as the lactams, amino acids and oligomers, will not be extracted under the effect of the electric current and will remain in the dilution compartment D.

According to a preferred embodiment of the invention, the process is carried out in a cell comprising at least two elemental electrodialysis cells mounted in electric series.

Thus, the concentration compartment C of one elemental cell will also be the concentration compartment C of the adjacent cell. Consequently, the diamine extracted across the cationic membrane and the diacid extracted across the anionic membrane of the adjacent cell will be present in the same medium and will form an amine salt.

Another application of the process of the invention is a process for purifying or extracting an amine salt from a liquid medium.

In point of fact, by adjusting the pH of the liquid medium, the amine functions of the amine salt will be protonated, and under the effect of the current the compound containing an amine function will cross the cationic membrane while the compound containing an acid function will migrate towards the concentration compartment $C^-$ across the aninoic membrane. These two compounds extracted from the starting medium will recombine in the common concentration compartment C of two adjacent cells to reform the amine salt, in a form purified or separated from other compounds which may be contained in the starting liquid medium.

The process of the invention is preferably used for the separation and extraction of the diamine monomers contained in the medium of hydrolysis of polyamides. For this application, the pH of the liquid medium is advantageously between 6 and 9, preferably between 7 and 8.The pH of the liquid medium can be adjusted by any known means, such as by addition of basic or acidic compounds.

This process finds an application in particular in the separation, recovery and purification of the monomers produced by thermal hydrolysis completed by an enzymatic hydrolysis of polyamides containing, in particular, a polyhexamethylene adipamide. This polyamide can be in a mixture with other polyamides such as polycaprolactam or can be in the form of copolyamide.

The process of the invention makes it possible, in this application, to separate hexamethylenediamine and adipic acid from the other monomers originating, for example, from polycaprolactam, such as aminocaproic acid or caprolactam, as well as from the oligomers which are not fully hydrolysed or from by-products of the hydrolysis.

The concentrations of compounds to be extracted or separated, in particular of amine salts or amine and acid monomers in the liquid medium are not critical. However, these concentrations may advantageously be between 0.2 mol/l and 2 mol/l, preferably 0.2 mol/l to 1 mol/l.

Standard electrodialysis devices are suitable for carrying out the process.

Thus, a suitable electrodialysis device for carrying out the process consists of various compartments delimited respectively by cationic membranes and anionic membranes. These compartments are divided into dilution compartments D which become depleted in compound to be separated, i.e. in diacids and diamines or salts of corresponding amine in the process of the invention, and into concentration compartments C which, in contrast, become enriched in compounds to be separated.

The reason for this is that, under the action of the electric field, the protonated amines in the solution to be treated migrate towards the cathode, leaving the compartment D in which they are found, across a cation-exchange membrane (cationic membrane). When they have passed into the next compartment C, they cannot leave it on account of the presence of the next anion-exchange membrane (anionic membrane). Simultaneously, the acid compounds migrate towards the anode, crossing an anionic membrane, and pass into an adjacent compartment $C^-$, which they can then not leave on account of the presence of the next cationic membrane.

Two adjacent compartments C and D form an electrodialysis cell. An electrodialyser includes a stack of several cells. This number of cells per electrodialyser is generally as high as possible. For example, this number can advantageously range between 5 and 500 cells.

In practice, the anionic and cationic membranes are arranged alternatively in a system of filter-press type.

The homopolar membranes used in the process of the invention are divided into two major families, depending on their method of manufacture.

There are, firstly, the heterogeneous membranes, prepared from ion-exchange resins, mixed with a binder such as poplyvinyl chloride, polyethylene or the like. The assembly thus formed can coat a frame such as, for example, a polyester or polyacrylonitrile fabric.

There are also the homogeneous membranes, obtained by introducing a functional group onto an inert support, by chemical or radiochemical grafting. The chemical method, which is most commonly used, generally consists in functionalizing a latex of a polymer containing aromatic rings, such as styrene/divinylbenzene or styrene/butadiene. The latex thus functionalized then serves for coating a frame as for the heterogeneous membranes. The radiochemical method generally includes the grafting, under the influence of radiation, of an aromatic compound, such as styrene, onto an inert support such as a sheet of polyethylene or of polytetrafluoroethylene. The aromatic ring is then functionalized as in the chemical method.

The cation-exchange membranes (cationic membranes) contain strong acid groups, usually sulphonate groups, or weak acid groups, usually carboxylate groups. More rarely, the acid groups can be $PO_3^{2-}$, $HPO_2^-$, $AsO_3^{2-}$ or $SeO_3^-$.

The anion-exchange membranes (anionic membranes) contain strong basic groups, usually quaternary ammonium groups, or weak basic groups, usually amine groups. More rarely, the basic groups can be quaternary phosphonium groups or sulphonium groups.

In the present process, the cationic membranes preferably contain strong acid groups and, among these, preferably sulphonate groups, and the anionic membranes preferably contain strong basic groups and, among these, preferably quaternary ammonium groups.

According to another embodiment of the invention, the electrodialysis is carried out by arranging a bipolar membrane in each common concentration compartment C.

The bipolar membrane is an assembly of two membranes, one cationic, the other anionic. When the membrane is subjected to a sufficient electric field, the water of solvation at the membrane interface becomes dissociated into $H^+$ and $OH^-$ ions, which migrate respectively towards the cathode, crossing the cationic face, and towards the anode, crossing the anionic face. As bipolar membranes, mention may be made, for example, of the membranes sold by the companies Aqualytics, Tokuyama Soda and FuMaTech.

Thus, in this embodiment, the electrodialysis device consists of various compartments delimited respectively by cationic membranes, bipolar membranes and anionic membranes. These compartments are divided into a dilution compartment D which becomes depleted in compounds to be separated, an acid compartment $C^-$ and an amine compartment $C^+$ in which the acid and the amine extracted from the compartment D are respectively concentrated.

In point of fact, under the action of the electric field, the protonated amine migrates towards the cathode, leaving the compartment D in which it is found, across a cation-exchange membrane (cationic membrane). When it has passed into the next compartment $C^+$, the amine is deprotonated by the supply of $OH^-$ ions originating from the anionic face of the bipolar membrane, within which the dissociation of water takes place under the effect of the electric field. The amine is thus regenerated.

Simultaneously, the carboxylate (adipate) ions migrate towards the anode, leaving the compartment D in which they are found, across an anion-exchange membrane (anionic membrane). When they have passed into the next compartment ($C^-$), they are protonated by the supply of $H^+$ ions originating from the cationic face of the bipolar membrane. The three adjacent compartments $C^+$, $C^-$ and D form an electrodialysis cell. An electrodialyser includes a stack of several cells. For example, this number can advantageously range between 5 and 300 cells.

Besides the membranes, the electrodialyser includes, of course, a cathode and an anode. The anode is made of materials conventionally used in electrodialysis, for example graphite or nickel, titanium coated with precious metals or oxides of precious metals, in particular platinized titanium. The cathode is also made of materials conventionally used in electrodialysis, for example graphite, stainless steel or nickel.

The electrodialyser is fed with the aqueous solution to be treated. It is also necessary to circulate a solution of an anolyte at the anode and a solution of a catholyte at the cathode. These solutions often constitute a single electrolyte solution. In the present process, a single electrolyte circuit is suitable. The role of the electrolyte solution is to ensure a sufficient conductivity. Preferably, this conductivity will be equal to or greater than 20 millisiemens per centimetre (mS/cm), without this lower limit being considered as critical for carrying out the present process.

The electrolyte used is an ionizable compound such as a salt, an acid or a base. The electrolyte is preferably chosen from non-electroactive compounds. Thus, for example, it is preferable industrially not to use chlorides which generate chlorine at the anode.

As examples of electrolytes, mention may be made of neutral salts such as sulphates, acids such as sulphuric acid, and bases such as sodium hydroxide.

The voltage or the current density applied to the electrodialyser without a bipolar membrane must be such as to avoid polarization of the system, i.e. a dissociation of water under the effect of an over-intense electric field. As an example, the current densities used are about $0.15$ $kA/m^2$; this value should not be considered as a maximum value. In the case of an electrodialysis with a bipolar membrane, the current density applied is generally higher in order to polarize the said membrane. Thus, the current densities applied are generally between 0.2 and 1.5 $kA/m^2$, preferably between 0.2 and 0.5 $kA/m^2$. Cells comprising compartments between 0.5 mm and 2 mm in thickness, and preferably between 0.6 mm and 1.5 mm in thickness, are preferred.

The temperature at which the process of the invention is carried out is in a range which is compatible with the stability of the membranes, since, although, in principle, high temperatures are favourable, by increasing the electrolytic mobility and reducing the viscosity of the solution to be treated, the increase in temperature reduces the lifetime of the membranes. The process will thus preferably be performed at a temperature below or equal to 70° C. and more particularly between 20° C. and 60° C.

The electrodialyser can function in different ways. Firstly, it can function in continuous mode (functioning in direct passage), the solution to be treated continuously crossing the stack; several stages are then arranged in hydraulic series if the level of treatment to be obtained requires it. It can also function in batchwise mode (functioning in recirculation), the solution to be treated recirculating in a tank until the desired level of treatment is obtained. Lastly, it can function in direct passage with partial recirculation.

Moreover, in order to obtain good functioning of the electrodialysis, the electrical conductivity of the solutions contained in the concentration compartments $C^+$ and $C^-$ must be sufficient. Thus, in the embodiment with a bipolar membrane, the diamine solution present in the compartments $C^+$ can have a conductivity which is too low to allow correct functioning of the electrodialysis cell. In this case, the electrical conductivity may be increased by adding a small amount of electrolyte. The choice of the electrolyte must be made as a function of its non-reactivity with the amine and the possibility of separating it easily from the amine in order to recover this amine in a state of maximum purity.

This increase in the conductivity is also valid for the solution in the compartment $C^-$ containing the acid compound.

In addition, the volume of the solution circulating or contained in the compartments $C^-$, in particular in the case of the electrodialysis with a bipolar membrane, must be sufficient to have a concentration of acid compounds at the end of the electrodialysis or leaving the compartment which is less than the saturation concentration of the said acid compound, at the operating temperature of the cell. Thus, any precipitation of acid compounds is avoided.

Moreover, it is preferable to filter the liquid medium to be treated before feeding it into the electrodialysis cell, in order to avoid blocking the membranes.

Other aims, advantages and details of the invention will emerge more clearly on reading the examples, given solely as a guide and with no limiting nature being intended.

EXAMPLE 1

The electrodialyser is a stack of 10 cells with an active surface of 2 dm$^2$, each cell being composed of 2 compartments:

- a compartment D limited on the anode side by an anion-exchange membrane sold by the company Tokuyama Soda under the trade name Neosepta AMX, and on the cathode side by a cation-exchange membrane sold by the same company under the name Neosepta CMX,
- a compartment C limited on the anode side by the above cationic membrane, and on the cathode side by the anionic membrane of the adjacent cell.

The electrolyte circulating at the level of the electrodes is a solution of $Na_2SO_4$ with an electrical conductivity of 20 mS/cm.

The solution feeding the compartments C is a solution containing 5 g/l of NaCl.

The temperature at which the process is carried out is room temperature, of about 22° C.

The voltage set between the electrodes is 18 volts.

The solution fed into the compartment D has the following composition:

| | |
|---|---|
| adipic acid | 7.25% by weight (0.5 mol/l) |
| hexamethylenediamine (HMD) | 5.99% by weight (0.52 mol/l) |
| 6-aminocaproic acid | 7.30% by weight |
| caprolactam | 5.65% by weight |
| pH | 8.4 |

This composition corresponds to the one obtained by total hydrolysis of a mixture of PA 6.6 and PA 6.

This solution is subjected to an electrodialysis for 30 minutes.

The solution in the compartment C analyzed after stopping the electrodialysis has the following composition (with the exception of the NaCl):

| | |
|---|---|
| adipic acid | 1.18% |
| HMD | 0.67% |
| 6-aminocaproic acid | <0.04% |
| caprolactam | <25 ppm |

These results clearly show the effect of separation of the adipic acid and of the hexamethylenediamine, i.e. of the hexamethylenediamine adipate salt relative to the caprolactam and to the 6-aminocaproic acid.

The faradic yield relative to the HMD is about 84%, whereas it is about 100% relative to the adipic acid.

EXAMPLE 2

This example was carried out under the same conditions as Example 1, but with a starting solution having the following composition:

| | |
|---|---|
| adipic acid | 3.63% by weight (0.25 mol/l) |
| hexamethylenediamine | 2.99% by weight (0.26 mol/l) |
| 6-aminocaproic acid | 3.65% by weight |
| caprolactam | 2.83% by weight |

The electrodialysis was continued to the point of depletion of the HMD and adipic acid in the solution contained in the compartment D.

The solution recovered in compartment C has the following composition:

| | |
|---|---|
| adipic acid | 3.30% |
| HMD | 2.36% |
| 6-aminocaproic acid | <0.02% |
| caprolactam | <0.01% |

A hexamethylenediamine adipate salt containing less than 3500 ppm of 6-aminocaproic acid and 1.7% of caprolactam is thus obtained.

EXAMPLE 3

This example was carried out in an electrodialysis cell comprising two compartments separated by a cationic membrane sold by the company E.I. Du Pont de Nemours under the trade name Nafion® 324.

The anodic compartment initially contains 300 ml of a solution resulting from the hydrolysis with sodium hydroxide of polyamide 6.6 and having the following weight composition:

| | |
|---|---|
| sodium adipate | 139 g/l (0.73 mol/l) |
| hexamethylenediamine | 83 g/l (0.73 mol/l) | the pH of the solution is initially 12.5.

The cathodic compartment initially contains 250 cm$^3$ of a sodium hydroxide solution at 5% by weight.

The electrodialysis is carried out at 65° C. with a current density of 20 A/dm$^2$.

The HMD concentration in the cathodic compartment is measured as a function of time, as is the pH of the solution in the anodic compartment D.

The results are indicated in the table below.

| Time (min) | Anolyte pH | Catholyte [HMD] |
|---|---|---|
| 0 | 12.5 | not detected |
| 240 | 11.5 | not detected |
| 340 | 11.0 | not detected |
| 360 | 10.5 | 0.19 mol/l |
| 380 | 9.0 | 0.24 mol/l |
| 400 | 6.5 | 0.29 mol/l |

After electrolysis for 400 minutes, 40% of the HMD initially present in the anolyte have passed into the cathodic compartment.

EXAMPLE 4

The electrodialyser used consists of a stack of 5 cells with an active surface of 2 dm$^2$, each composed of 3 compartments denoted as follows:

a compartment (D): limited on the anode side by an anion-exchange membrane sold by the company Tokuyama Soda under the trade name Neosepta AHA-2, and on the cathode side by a cation-exchange membrane of the trade name Neosepta CMB, a compartment (C⁻): limited on the cathode side by an anionic membrane, and on the anode side by the cationic face of a bipolar membrane of trade name Aqualytics, a compartment (C⁺): limited on the anode side by the cationic membrane, and on the cathode side by the anionic face of the bipolar membrane.

The anode consists of platinized titanium. The cathode is made of stainless steel.

The electrolyte consists of an aqueous solution of sodium sulphate at 160 g/l. The circulation flow rate at the electrodes is 2×100 l/h. The volume is 5 l.

The compartment C⁺ is initially filled with 5.2 litres of a sodium hydroxide solution at 5 g/l.

The compartment C⁻ is initially filled with 7.5 litres of a 1% nitric acid solution.

The compartment D is initially filled with 4 kg of a solution having the following weight composition:

| | |
|---|---|
| hexamethylenediamine adipate | 12.5% |
| caprolactam | 5.5% |
| 6-aminocaproic acid | 7% |
| water | 75% |

The recirculation flow rate of the solutions is set at 80 l/h for the circuits in the compartments C⁺ and C⁺, and at 60 l/h for the circuit in the compartment D.

The electrodialysis is carried out in batchwise mode (functioning in recirculation), at an average temperature of 42° C. The current is set at 5 A, i.e. a current density of 0.25 kA/m².

After operating for 248 minutes, the conductivity of the compartment D has gone from 22.9 to 1.8 mS/cm.

The final volume of the compartment C⁺ is 5.86 litres. The hexamethylenediamine concentration is 0.254 mol/l, i.e. a degree of extraction or recovery of 78%.

The final volume of the compartment C⁻ is 7.92 litres. The adipic acid concentration is 0.183 mol/l, i.e. a degree of extraction or recovery of 76%.

The faradic yield is between 75 and 77%.

What is claimed is:

1. Process for extracting, in liquid medium, compounds comprising at least two protonatable amine functions, comprising protonating the amine functions by adjusting the pH of the medium and separating the compounds by passing them through a cationic membrane under the effect of the electric field.

2. Process according to claim 1, wherein the compound comprising at least two protonatable amine functions is an amine salt.

3. Process according to claim 2, wherein amine salt comprises amine adipates or amine phthalates.

4. Process according to claim 1 wherein the amine compound is hexamethylenediamine.

5. Process according to one of claims 1 to 4, characterized in that the electrodialysis comprises at least one anionic membrane and at least one cationic membrane forming an elemental electrodialysis cell, with a dilution compartment (D) and concentration compartments (C).

6. Process according to claim 5, wherein the electrodialysis comprises at least two elemental cells mounted in electrical series.

7. Process according to claim 6, comprising protonating the amine functions of an amine salt contained in a solution, feeding said solution into the compartment (D), and passing, under the effect of electric current, into the common concentration compartments (C), across the cationic and anionic membranes respectively, the protonated amine and the anion of the amine salt, and reforming the extracted amine salt said compartments (C).

8. Process according to claim 6, wherein the electrodialysis comprises a bipolar membrane arranged in the compartment (C) located between two elemental electrodialysis cells mounted in electrical series.

9. Process according to claim 1, wherein the liquid medium comprises monomers obtained by depolymerization of polyamides.

10. Process according to claim 9, wherein the liquid medium is obtained by hydrolysis of polyamides.

11. Process according to claim 10, wherein the liquid medium is obtained by thermal hydrolysis followed by an enzymatic hydrolysis of polyamides.

12. Process according to claim 1, wherein the polyamides comprise polyamide 6.6, polyamide 6, polyamide 4.6, polyamide 11, polyamide 12, semi-aromatic polyamides of the polyphthalamide type, mixtures thereof or copolyamides thereof.

13. Process according to claim 1, wherein the molar concentration of the compounds to be separated in the liquid medium is between 0.2 mol/l and 2 mol/l.

14. Process for producing polyamide monomer, comprising hydrolysing polyamides in order to obtain a liquid medium containing the monomers of starting polyamides, and separating the diacid, diamine and amino acid or lactam monomers by electrodialysis of the liquid medium; and extracting from the liquid medium compounds comprising at least two protonatable amine functions, comprising protonating the amine functions by adjusting the pH of the medium and separating the compounds by passing them through a cationic membrane under the effect of the electric field;

wherein the electrodialysis comprises at least one anionic membrane and at least one cationic membrane forming an elemental electrodialysis cell, with a dilution compartment (D) and concentration compartments (C) and at least two elemental cells mounted in electrical series.

15. Process according to claim 14, wherein the hydrolysis is a thermal hydrolysis in neutral medium followed by an enzymatic hydrolysis.

* * * * *